United States Patent [19]
Michelson

[11] Patent Number: 5,009,661
[45] Date of Patent: Apr. 23, 1991

[54] PROTECTIVE MECHANISM FOR SURGICAL RONGEURS

[76] Inventor: Gary K. Michelson, 438 Sherman Canal, Venice, Calif. 90291

[21] Appl. No.: 341,849

[22] Filed: Apr. 24, 1990

[51] Int. Cl.⁵ .................................... A61B 17/16
[52] U.S. Cl. .................................. 606/170; 606/205
[58] Field of Search ............... 606/79, 83, 167, 170, 606/172, 205, 206, 208, 209

[56] References Cited
U.S. PATENT DOCUMENTS

| | | | |
|---|---|---|---|
| 1,127,948 | 2/1915 | Wappler | 606/170 X |
| 4,122,856 | 10/1978 | Mosior et al. | 606/170 |
| 4,662,371 | 5/1987 | Whipple et al. | 606/170 |
| 4,760,848 | 8/1988 | Hasson | 606/222 X |

Primary Examiner—Robert A. Hafer
Assistant Examiner—Kerry Owens
Attorney, Agent, or Firm—Lewis Anten

[57] ABSTRACT

A protective spring mechanism is employed to protect the jaws of a surgical rongeur, thereby protecting the fragile parts of the activating mechanism from excessive peak loads and preventing breakage.

12 Claims, 4 Drawing Sheets

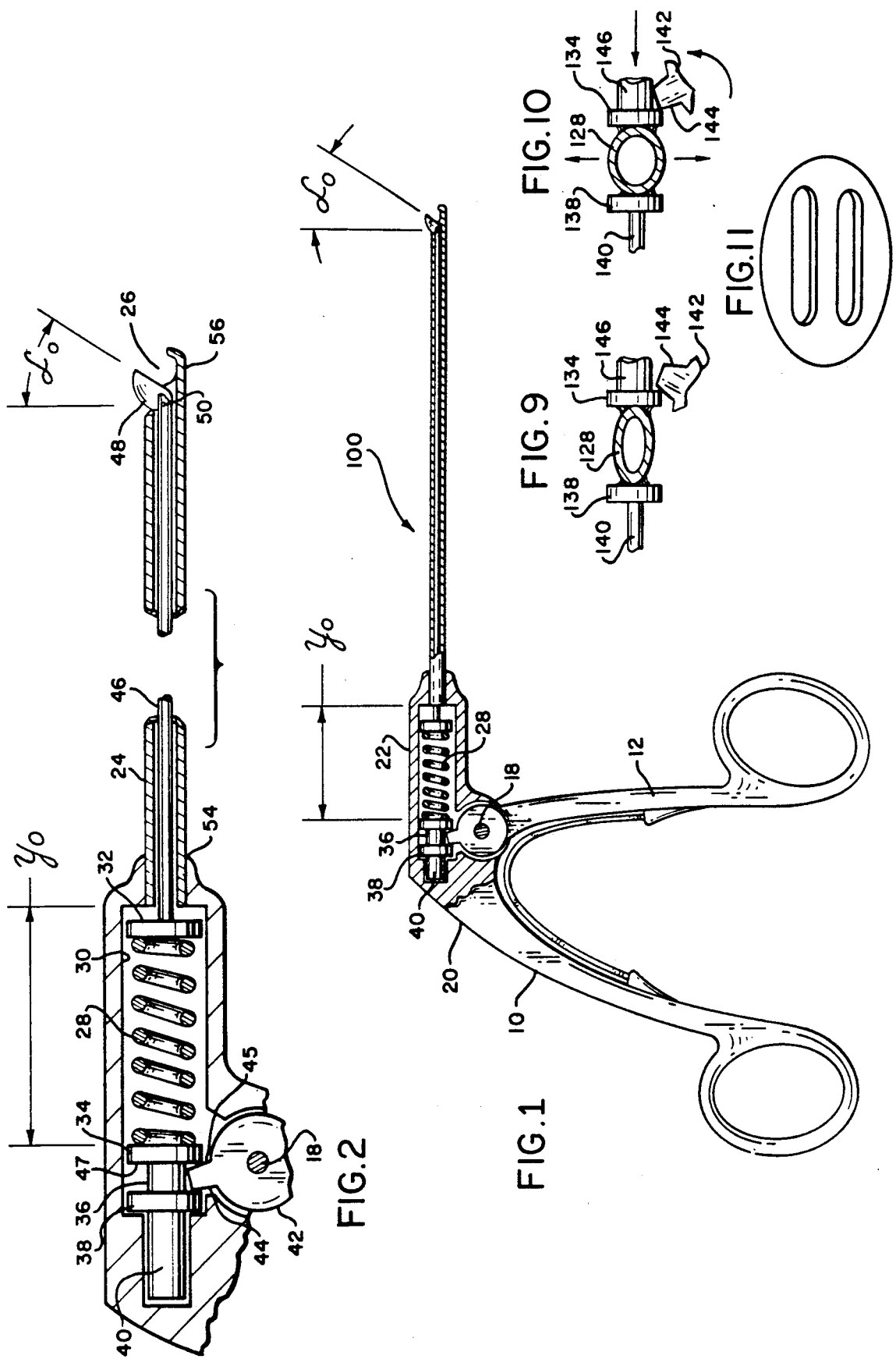

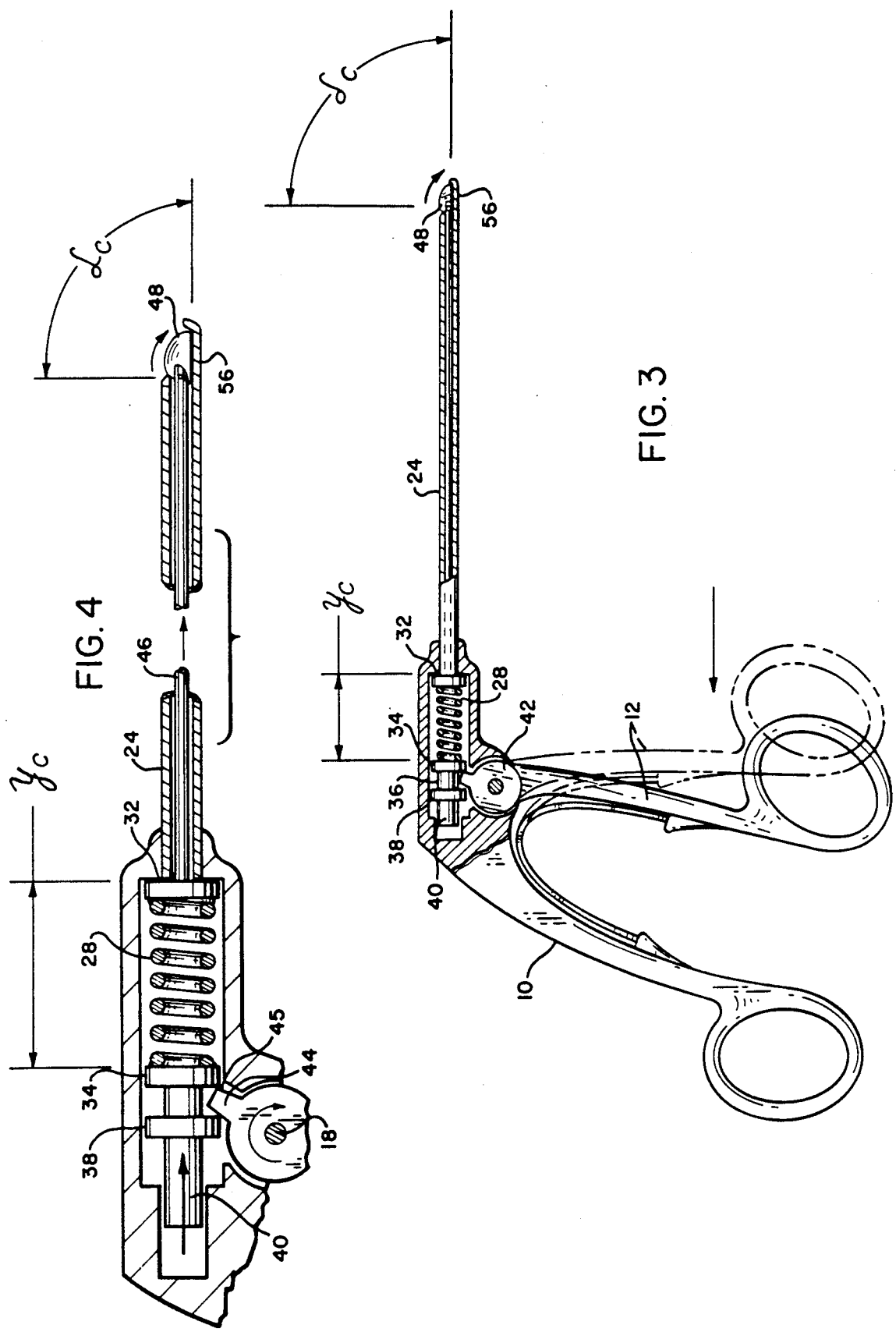

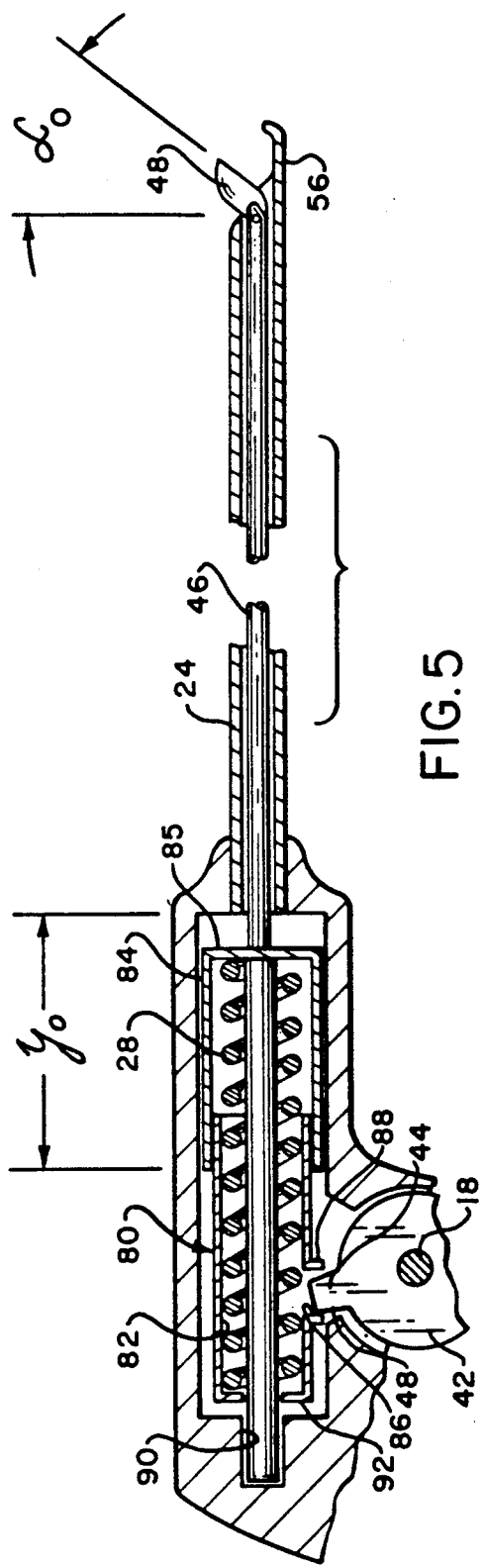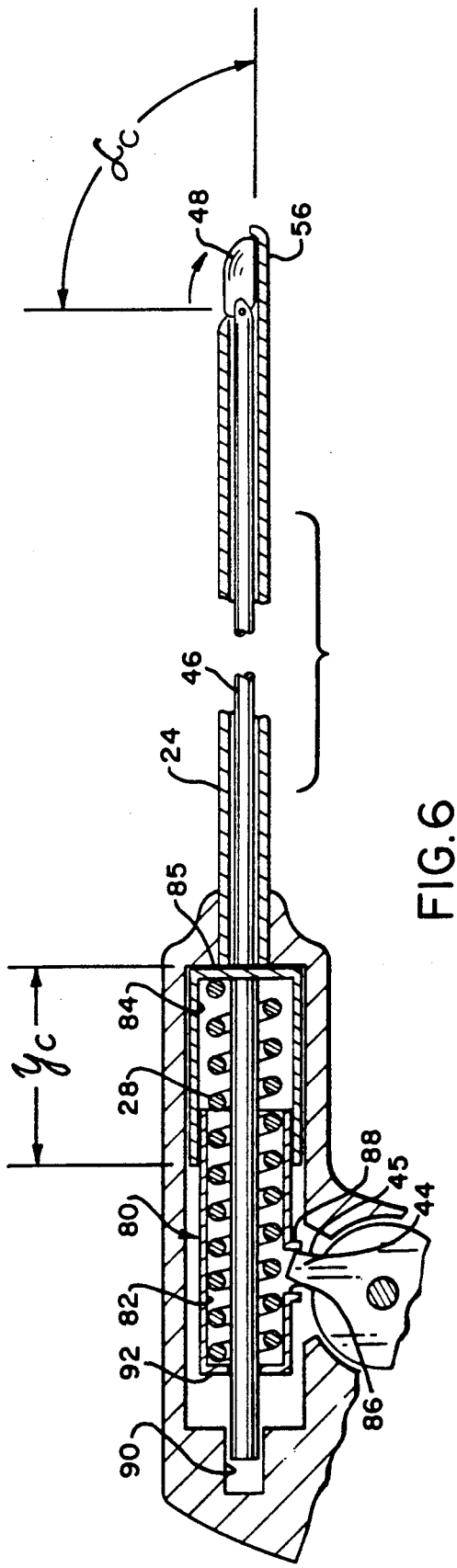

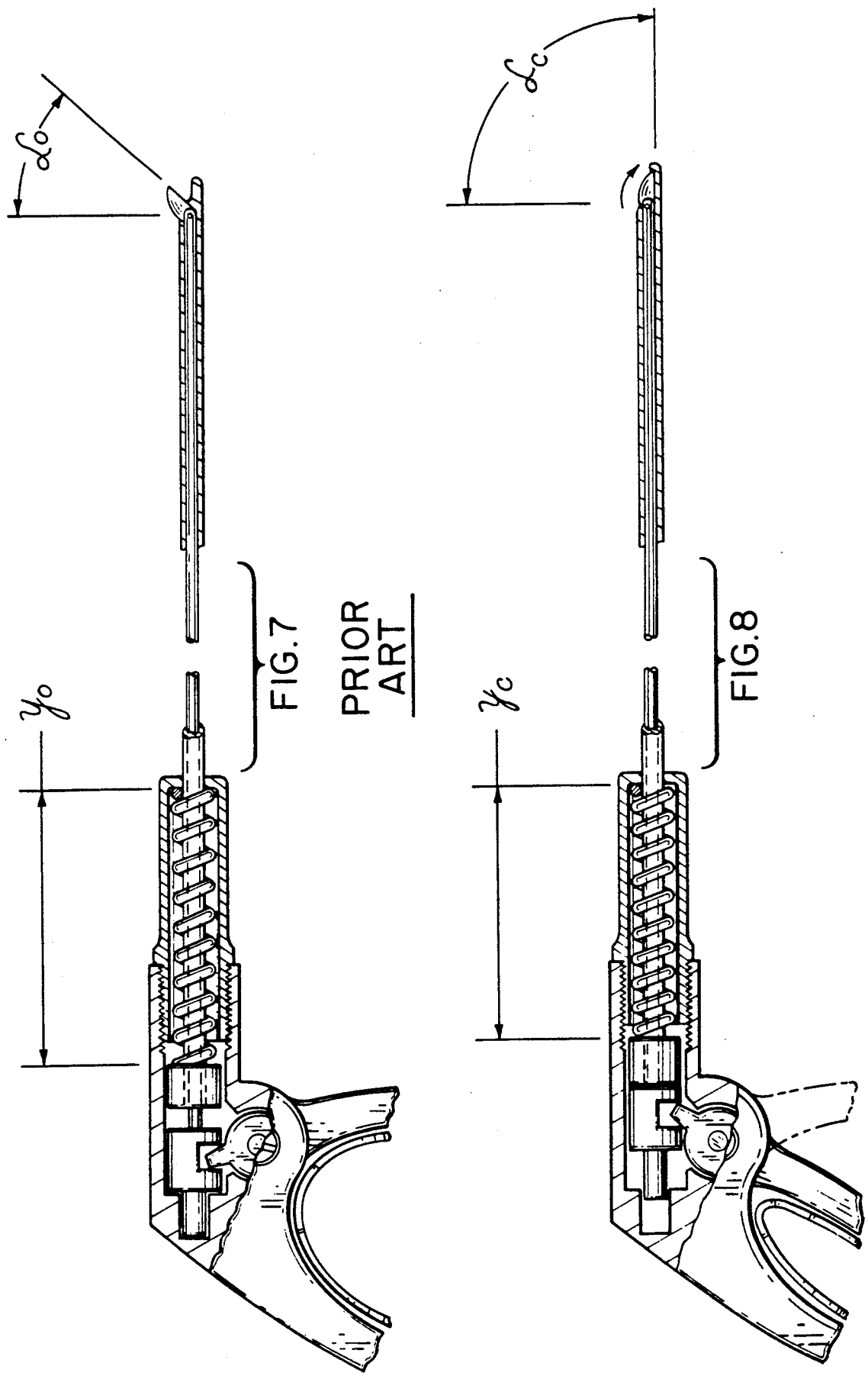

PROTECTIVE MECHANISM FOR SURGICAL RONGEURS

BACKGROUND

Rongeurs are surgical instruments designed to bite off and hold fragments of tissue. They have jaws, in the form of a cup, that can be opened and closed. They are made in a vast variety of sizes and shapes consistent with their intended purposes. For example, those designed to remove bone are generally quite strong and deliberately designed so that the biting area times the force generated by that biting is considerably less than the supporting area and the ability of the supporting structures to withstand such forces without damage. Other rongeurs, such as those used in operative arthroscopy (surgery performed on a joint through a small puncture using an illuminated telescope like device about the size of a pencil and various instruments inserted through a similar puncture) or an operative endoscopy (same as above but anywhere within the body rather than just a joint), are designed to only bite softer tissues and may be significantly constrained in their design and dimensions by their intended site of use. For example, those rongeurs used to remove tissue from a temporomandibular joint (hinge joint of the jaw) must, because of the small size of the joint, be rather small and correspondingly delicate.

However, as a practical matter for any given hardness of tissue to be bitten, there is a minimum thickness needed to support the biting edge regardless of the size of the bite. Since these rongeurs bite around a piece of tissue using their sharpened perimeters and do not punch out the tissue over the entire surface area, then the thickness and strength of the cutting edge and supporting infrastructure is dictated by the hardness and thickness of the tissue to be cut. Therefore, the first problem that arises with the design of a rongeur is that as the tip of the instrument gets smaller, the needed edge wall thickness decreases at a lesser rate such that one would end up with a set of cutting edges that were so close together that there would be virtually no area in between to be cut. Furthermore, while that would already be undesirable, to make an instrument small enough for the purpose intended, even a rongeur reduced to only biting edges and with no central area might actually be still too large if one attempted to preserve the optimal edge thickness in regards to the tissue to be removed. As a practical matter therefore, small rongeurs such as those used to perform operative arthroscopy are limited to the purpose of removing soft tissues only.

When an unexpectedly hard piece of tissue or bone is accidentally bitten during the surgery, then the instrument may be damaged or destroyed by a failure at either the tip or at either the proximal or distal axis pins.

At present, in an attempt to protect the delicate working tips of these rongeurs, some rongeurs have been constructed so that some other area than the tip will fail when overloaded, thus preserving the integrity of the tip. This would appear to be logical as the entire instrument only exists to make the tip work and as a practical matter when the tips are damaged the instrument is generally not repairable. The most likely candidate to be designed for first failure would then seem to be the distal pin. That is because empirically these structures already have a high failure rate and because of their requisite small size, dictated by the small dimensions of the working tip, they are rather weak to begin with. If the tip is protected by failure of the distal pin, then the instrument can be repaired by pushing out the distal pin and replacing it with a new pin, a procedure that can be performed at a factory repair center. However, this is unacceptable as a failure of the distal pin occurring inside the human body and particularly within a joint might result in loose steel fragments within that joint which could severely damage the joint or result in further or additional surgery to remove such fragments. Therefore, most instrument makers have elected to assure that any instrument failure occurs outside the joint and have done so by markedly weakening the proximal pin or equivalent mechanism. Unfortunately, to be reasonably assured that this will indeed be the point of failure, it is necessary to make the proximal pin considerably weaker than the already very weak (by the necessity of the size limitations) distal pin resulting in a significantly compromised and weak instrument that fails easily and must be returned to the factory service center repeatedly for repair at a not insignificant cost.

One approach employed to prevent the damage to the tip has involved the insertion of a spring relief mechanism interposed between the handle and the tip sold under the Dyonics trademark. While such a spring mechanism does prevent the breaking of the tip, as shown in FIGS. 7 and 8, the entire tip moves forward upon application of excessive pressure. The movement of the tip results in the undesirable problem of the user either balancing the movement of the tip by withdrawing it slightly, or compensating for the forward movement during the grasping. Either of these approaches are undesirable. In addition, the above prior device was complicated, difficult and expensive to manufacture.

SUMMARY OF THE PRESENT INVENTION

In the present invention a safety spring mechanism is interposed between the activating means, typically the handle, and the drive mechanism for closing the jaws for the purpose of protecting the instrument from failure due to peak stress overload of the jaws. In effect, the safety spring mechanism is part of the drive shaft itself, and limits the force that the drive shaft itself can apply to the jaws. The releasable safety spring mechanism protects the instrument from repeated high, but less than overload, stresses thereby delaying fatigue failure and prolonging the instrument's life. The safety spring relief mechanism absorbs excessive pressures that would otherwise be applied to the jaws, but does not require the jaws to be displaced during use.

OBJECTS OF THE PRESENT INVENTION

It is an object of the present invention to provide an improved medical instrument which is less likely to be damaged.

It is another object of the present invention to provide for a protective mechanism for a medical instrument that will protect the device from unacceptable high peak stresses making it more reliable.

It is still another object of the present invention to provide for a protective mechanism for a medical instrument that is easier to use.

It is yet another object of the present invention to provide for a protective mechanism for a medical instrument that will provide for greater patient safety by avoiding metal failure and fragmentation within the body.

It is still another object of the present invention to provide for a protective mechanism for a medical instrument which can be more inexpensively made.

It is yet another object of the present invention to provide a protective mechanism for a rongeur that can be used in the same manner as present rongeurs.

These and other objects of the present invention will be apparent from a review of the following specification and the accompanying drawings, of which the following is a brief description.

BRIEF DESCRIPTION OF THE DRAWINGS

FIG. 1 is a partial sectional view of the rongeur of the present invention.

FIG. 2 is an expanded partial sectional view of the upper portion of the present invention.

FIG. 3 is a side partial sectional view of the rongeur of the present invention with the handle in its retracted position.

FIG. 4 is an expanded view of the protective spring mechanism of FIG. 3.

FIG. 5 is an expanded partial side sectional view of the upper portion of an alternative embodiment of the present invention in its forward position.

FIG. 6 is an expanded partial side sectional view o the upper portion of the embodiment of FIG. 5 with its handle closed.

FIG. 7 is a side partial sectional views of a prior art rongeur with a spring release mechanism.

FIG. 8 is the prior art rongeur of FIG. 7 in a closed position.

FIG. 9 is a partial sectional view of an alternative resilient member arrangement with the resilient member in its normal, uncompressed position FIG. 10 is a partial sectional view of an alternative resilient member arrangement with the resilient member in its compressed position.

FIG. 11 is a perspective view of an alternative embodiment of a resilient member.

DETAILED DESCRIPTION OF THE DRAWINGS

Referring to FIG. 1-4, the rongeur 100 of the present invention, is shown. The rongeur 100 consists of pivotal rear handle 10 and forward handle 12 having conventional finger openings 14 and 16 at their ends. The rear handle 10 is fixed and movable relative to forward handle 12 which is pivotal at its upper end about pin 18 in the frame 20.

The frame 20 houses the spring drive housing 22. The spring drive housing 22 is connected to hollow shaft 24 terminating tip 26. The distal end of the hollow shaft 24 has an extension portion 56 that forms the lower fixed jaw of the tip 26 and has a sharpened portion about its periphery. The spring drive housing 22 encloses a coil spring 28 within the tubular hollow 30 formed between forward disc 32 and rear disc 34. Extending from the rear disc 34, on the side opposite the coil spring 28, is a shaft 36, a second disc 38 and a further extension of shaft 40.

The top portion of pivotal handle 12 has an attached circular disc 42, rotatable about pin 18. At the upper portion of circular disc 42 is a projection 44. The projection 44 fits between the space formed between rear disc 34 and the second disc 38.

Projecting longitudinally from the front disc 32 is drive shaft 46, which is connected to upper jaw 48 of the tip 26. The extension rod 46 is connected to upper jaw 48 through pin 50 to create a pivotal force on upper jaw 48.

The device operates as follows. The rongeur 100 is held in the palm of the hand with the thumb held in opening 14 and the third finger of the hand in the opening 16 in forward handle 12. The tip 26 is inserted into the wound through a previously made opening. When tissue is either observed or felt to be between the upper jaw 48 and the lower jaw 56 of the tip 26 the pivotal forward handle 12 is pulled rearwardly towards handle 10.

The pulling of the forward handle 12 rearward causes the circular disc 42 to rotate about pin 18, in turn causing projection 44 to rotate clockwise. The rotation of projection 44 causes the forward edge 45 of the projection 44 to push against the rear edge 47 of forward disc 34, driving the forward disc 34 forward.

In the absence of a sufficient compression force on coil spring 28, the force applied to the disc 34 is applied through spring 28 directly to forward disc 32, which in turn drives disc 32 and drive shaft 46 forward, causing upper jaw 48 to pivot closing the upper jaw 48 against lower jaw 56 and grasping and cutting the tissue between the jaws.

If the tissue or other substance is so hard a to prevent the jaws of the tip 26 from closing, then the coil spring 28 receives a sufficient compression force to compress the spring thereby preventing any additional force being applied to drive shaft 46. Thus, only a predetermined amount of force is permitted to be applied to the tip 26, determined by the compression force of the spring 28, preventing either pin 50 or pin 18 from breaking. The balance is absorbed by the coil spring 28.

Upon the surgeon releasing the pressure on the forward handle 12, the coil spring 28 causes the projection 44 to rotate counter clockwise, returning the handle 12 to its original position.

Referring to FIGS. 5 and 6, an alternative embodiment of the present invention is shown. In the alternative embodiment, the coil spring 28 is enclosed within a housing 80 formed by a rear closed inner hollow tube 82 and a slightly larger forward outer hollow tube 84. An open slot 86 is located on the lower portion of the rear hollow inner tube 82 proximate the projection 44. The front end of the slot 86 has a depending projection 88 for engagement with the forward edge 45 of the projection 44. Shaft 46 passes through an opening in the front wall 85 of the outer tube 84, through the opening in the coil spring 28 and through the rear inner tube 82, into guide slot 90. The transmission shaft 46 is rigidly attached to the rear wall 92 of the rear inner tube 82.

As before, pulling of the front handle 12 rearwardly, will cause the projection 44 to move in a clockwise direction, causing the forward edge 45 to press against the projection 88, as shown in FIG. 6. Since the transmission shaft 46 is fixed to the rear wall 92 of the inner tube 82, as the inner tube is driven forward, the transmission shaft 46 is also driven forward, closing the jaws 48 and 56. Once the pressure on the tip 26 exceeds a desired force, the spring 28 is compressed, thereby preventing the transmission of any additional pressure to the tip.

While the present invention has been described with regards to the preferred embodiment of the present invention in use with a rongeur with a tip mechanism activated by a push rod, it is possible to use the present invention with other rongeurs and medical instruments. For example, it could be used equally well with rods that push or pull, with cables or a solid slide mechanism. Further, it can work equally well with hand or power activated instruments.

Also, while in the preferred embodiment a coil spring is used for the safety spring mechanism, it is recognized that other absorbent resilient relief mechanisms may be devised instead of a coil spring. For example, an oval member is shown in FIGS. 9 and 10 serving in the same capacity as the coil spring of the preferred embodiment described previously. The oval member 128 is supported in the chamber between the front and rear discs 134 and 138. As shown in FIG. 9, when there is not sufficient force to compress the oval 128 the force is transmitted through the oval member as though it was solid. However, as shown in FIG. 10, when there is sufficient force exerted on the oval member, such as when the jaws 26 of the rongeur 100 can not close, then the oval member 128 deforms, absorbing the force rather than applying it to the jaws of the rongeur.

The oval 128 member can be made in a number of configurations, including, but not limited to, a football like spheroid, a hollow ball or other suitable configuration. The oval member 128 can be made with slots or other weakening devices to precisely control the amount of force required before the oval will deform. Also, the choice of the particular material, the thickness and angularity of the oval member can be made to control the resiliency of the oval member. For example, a thin spring steel would be appropriate for the oval member.

Other resilient spring mechanisms can also be used without departing from the concept of the present invention. Further examples include the use of a leaf spring, or back to back springs typically used in a wagon. Additionally, compressible solid resilient materials, could be used in place of coil spring or oval member, so that the material compresses and returns to its original dimensions. There are many plastics on the market that are readily available and that would have sufficient resiliency to deform and then return to their original shape. Additionally, pressure or hydraulic springs could also be devised which would serve the purpose of the resilient spring.

While the present invention has been described in its use as a rongeur, it is appreciated that other medical instruments that have jaws that open and close may employ the resilient safety mechanism of the present invention without departing from the inventive concept of the present invention. For example, scissors or other cutting instruments can incorporate such a safety mechanism.

What is claimed is:

1. A rongeur comprising a drive shaft having a cutting means proximate one end of said drive shaft, said cutting means responsive to movement of said drive shaft, said drive shaft movable responsive to a drive means for driving said drive shaft, a resilient member, said resilient member interposed between said drive means and said cutting means whereby force applied to said resilient member is transmitted to said drive shaft.

2. The rongeur of claim 1 in which said drive means includes a pivotable handle, whereby pivoting of said handle moves said drive shaft.

3. The rongeur of claim 1 in which said resilient member comprises a spring.

4. The rongeur of claim 1 in which said resilient member comprises a coil spring.

5. The rongeur of claim 1 in which said resilient means comprises a solid compressible member.

6. The rongeur of claim, 1 in which said resilient member is enclosed in a housing, said housing attached to said resilient member and responsive to said drive means.

7. The rongeur of claim 1 in which said rongeur has a handle and drive shaft, said drive shaft is responsive to movement of said handle.

8. The rongeur of claim 5 in which said solid compressible member is made of plastic 9. The claim rongeur of claim 1 in which said resilient member comprises an oval member said oval member being deformable upon excess force being applied to said oval member.

10. The rongeur of claim 10 in which said oval member is a football shape spheroid, said spheroid having slots therein for controlling the resiliency of said oval member.

11. The rongeur of claim 1 in which said cutting means comprises jaws having an upper jaw and a lower jaw said jaws having a normally open position and a closed position, said resilient member being incompressible when said jaws are open and compressible when a predetermined amount of force applied to said jaws exceeds a predetermined force.

12. The rongeur of claim 11 including a second resilient return member for returning said jaws to their normally open position resilient member return means returning said drive means.

* * * * *